(12) United States Patent
Covey

(10) Patent No.: US 6,409,692 B1
(45) Date of Patent: Jun. 25, 2002

(54) ANKLE FOOT ORTHOSIS DONNING DEVICE

(76) Inventor: Ann Marie Covey, 800 kennebec Rd., Hampden, ME (US) 04444

( * ) Notice: Subject to any disclaimer, the term of this patent is extended or adjusted under 35 U.S.C. 154(b) by 0 days.

(21) Appl. No.: 09/658,526

(22) Filed: Sep. 9, 2000

(51) Int. Cl.[7] .................................................. A61F 5/00
(52) U.S. Cl. .......................................... 602/5; 602/27
(58) Field of Search ..................... 602/5, 8, 10; 482/80; 36/7.5, 110

(56) References Cited

U.S. PATENT DOCUMENTS

| | | | |
|---|---|---|---|
| 2,283,595 A | * 5/1942 | Banister | 36/7.5 |
| 2,519,458 A | * 8/1950 | Hall | 36/7.5 |
| 2,810,213 A | * 10/1957 | Jonas | 36/7.5 |
| 3,012,702 A | 12/1961 | Van Der Vliet | |
| 3,976,059 A | 8/1976 | Lonardo | |
| 4,683,876 A | 8/1987 | Changras | |
| 5,135,450 A | * 8/1992 | Smith | 602/10 |
| 5,687,889 A | 11/1997 | Liden | |
| 5,927,573 A | 7/1999 | Votino et al. | |
| 5,974,701 A | 11/1999 | Busch | |

* cited by examiner

Primary Examiner—Michael A. Brown
(74) Attorney, Agent, or Firm—Shalom Wertsberger; Saltamar Innovations

(57) ABSTRACT

An orthopedic guide to aid in donning an ankle foot orthosis (AFO) is disclosed comprising an L-shaped channel and a rocker to allow the L-shaped channel to smoothly rotate generally about the L-shape joint when tilted. The horizontal portion of the L is weighted to urge the device to an upright position when at rest. A shoe and an AFO are placed in the L-shaped channel and a patient foot uses the vertical portion of the L to guide the patient foot into the shoe. In use the device tilts to create a natural rotation movement for the foot insertion, and places the foot and guides it in a more comfortable tilted position. A shoe tongue retainer clip is also disclosed to allow further ease in donning the shoe and AFO by enlarging the shoe opening and keeping the tongue out of the way.

17 Claims, 8 Drawing Sheets

ANKLE FOOT ORTHOSIS DONNING DEVICE

FIELD OF THE INVENTION

The invention relates in general to orthopedic guides, and more particularly to an apparatus for aiding a person in donning an ankle foot orthosis.

BACKGROUND OF THE INVENTION

An Ankle Foot Orthosis (hereinafter an AFO) is a medical device that assists patients who have lost at least partial control over the angle in which they can maintain their foot respective to their leg. Often, as a result of a stroke or some other medical conditions, those patients' foot can not be raised to avoid obstacles. This may be dangerous, since the patient can trip. The AFO thus holds the foot at a predetermined angle, usually around 90 degrees, to the leg. Common AFO's hold the patient's calf and foot, and inserted into a regular shoe. The shoe is then worn over the AFO and thus the AFO is invisible. However donning such an AFO is a hard task for many patients due to the reduced motor control, difficulty in bending down, reduced coordination and other physical limitations stemming from their condition.

The AFO generally has a foot portion and a calf portion, at about 90 degrees to each other. The foot portion is inserted into the shoe, and the patient puts his/her leg into the shoe in the usual manner. A band or other securing means is used to secure the calf portion to the patient's calf. Thus the patient's foot gains rigidity to avoid dropping the foot at an angle greater than 90 degrees.

The problem of donning an AFO is known, and several inventions have been made to assist patients in donning them. In U.S. Pat. No. 4,683,876, Changras teaches an orthopedic guide having a backing slab and two parallel sidewalls secured parallel thereto to define a channel in which an AFO is placed within a shoe. The shoe is then placed in the channel, so that the AFO calf portion rests against the backing slab. The patient grabs a handle attached to the device and slides his foot along the AFO using it to guide his/her foot into the shoe.

The '876 patent suffers from several disadvantages. It forces the patient to hold onto the orthopedic guide while performing the task of sliding the foot down the guide. The device is placed vertically, so it requires the patients' leg to follow such a vertical movement. This is often inconvenient and difficult, especially while attempting to hold the device steady. The Changras device is also unstable since the backing plate and extensions to the side walls are placed high on the device causing it to have a high center of gravity and making it prone to falling over on its back or side. The device also requires the use of a strap in order to stabilize the shoe in place. For a patient with motor control problem, this is often a difficult task to achieve.

U.S. Pat. No. 3,012,702 to Van Der Vliet describes a shoehorn having a flat base to hold the shoe in place. A flexible portion positioned above the rear portion of the shoe is adapted to engage the heel of a foot being inserted into the shoe. This device again does not solve the problem of easily locating the device with the shoe at a comfortable angle for placing the patient's foot into the shoe, and the flexible portion is likely to interfere with an AFO inserted into the shoe. Additionally, while using a shoehorn, the AFO will tend to turn and fail to maintain alignment with the shoe. Votino et al. in U.S. Pat. No. 5,972,573 disclose another shoehorn directed specifically to the physically handicapped. This device as well is likely to interfere with a shoe having an AFO attached thereto, and is large and bulky in comparison to the current invention.

Different gripper devices are contemplated in the likes of U.S. Pat. Nos. 5,974,701 to Busch and 5,687,889 to Liden. Those devices fall short of the desired results as they require precise manipulation of a gripper arm or hook, placed at the end of a long stick, all by a patient often suffering severe motor dysfunction.

There is therefore a clear and unsolved need for a stable, simple to operate device to assist a patient in donning an AFO, without requiring uncomfortable or hard to maintain body positions. The current invention aims to provide such a device.

SUMMARY OF THE INVENTION

In this application, the word cylindrical is not limited to a circular cylinder or shape, but should be construed as the surface traced by a straight line moving parallel to a fixed straight line and intersecting a fixed planar curve. Unless otherwise indicated, the direction extending along the foot portion away from the joint is commonly referred to as forward and the direction extending along the calf portion away from the joint is referred to as up. Correspondingly, back and down directions are construed as opposite to said forward and up directions respectively. Unless otherwise indicated, the word 'device' relates to one or more implementations of the current invention.

It is an object of the present invention to solve the problem and shortcoming described above and to provide an AFO donning device constructed of an L-shaped channel where the vertical leg of the L shaped channel forms a channel-like calf portion, and the horizontal leg of the L shaped channel forms a channel-like-foot portion. The connecting point of the foot portion and the calf portion is referred to as a joint in this application. Surfaces and volumes generally formed within the volume bound by the smaller of the two angles defined by the foot portion and the calf portion are referred to as being inside, and conversely surfaces and volumes defined by the larger of the two angles are referred to as being outside, the L-shape.

A rocker is provided on the outer or rear side of the L-shaped channel, at least near the joint. The rocker extends rearwardly from the back side of the joint area, and has a convexly arcuate rail 25, acting as a ground engaging surface. The rail is contoured to act as a cam to allow substantially smooth rotation of the L-shaped channel into an inclined position when tilted.

The foot portion of the L-shaped channel is weighted, preferably at its forward portion away from the joint. The weighting may be done by properly distributing the mass of the device, using different materials, adding a weight along the foot portion, preferably at a point distal to the joint, or by other known methods. The weight distribution should be sufficient so that when the device is positioned on the rail, the weight of the foot portion will bias and urge the device to an upright rest position in which the calf portion is in a substantially vertical orientation, and the foot portion is in a substantially horizontal orientation. Optionally, in resting position, the device should lean slightly backward to compensate for the weight of a shoe and an AFO placed is the L-shaped channel, or provide a more comfortable angle for positioning a patient's leg.

Preferably, an extended rail extends upwardly in continuation to the aforesaid rail, or integrated therewith. In the preferred implementation, the extended rail is formed as an integral extension of the rocker, and extends upward and backward of the joint area to form a rocker extension. By adapting the extended rail cylindrical shape to increase the distance of the joint from the ground as the device is tilted, an eccentric cam is created. The eccentric cam further increases the moment of the added weight of the foot portion and thus further biases the propensity of the device to return to an upright rest position.

Optionally, the rocker may depend forwardly and downwardly from the joint area towards the distal end 15 of the foot portion to form a resting rail 30. Such a resting rail is helpful for example if an increased height or a specific rocking motion is desired.

To further enhance the invention, a shoe tongue retainer is disclosed. The shoe tongue retainer generally comprises a short C-shaped clip 202, where one end of the clip is bent or formed to roughly conform to the shoe toe, and the other end is formed as a hook to engage and maintain the tongue of a shoe at a forwardly folded position. This tongue retainer is used to increase the shoe opening during foot insertion, and may be easily removed when not needed, as described below.

SHORT DESCRIPTION OF THE DRAWINGS

DETAILED DESCRIPTION

Figure 1:
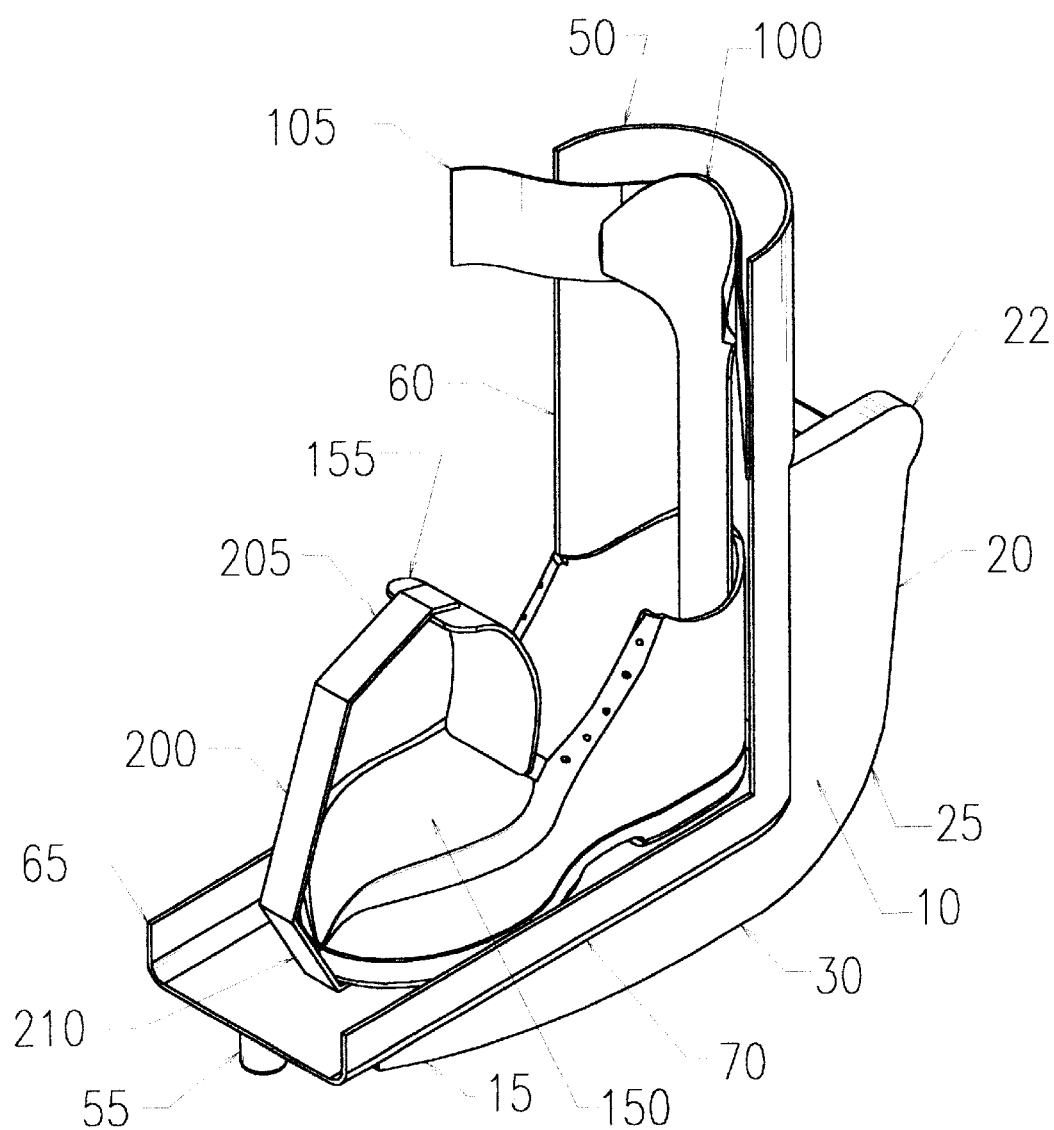
FIG. 1 depicts a schematic isometric view of one preferred implementation of the device, showing a shoe and an AFO in place for foot insertion.
Figure 2:
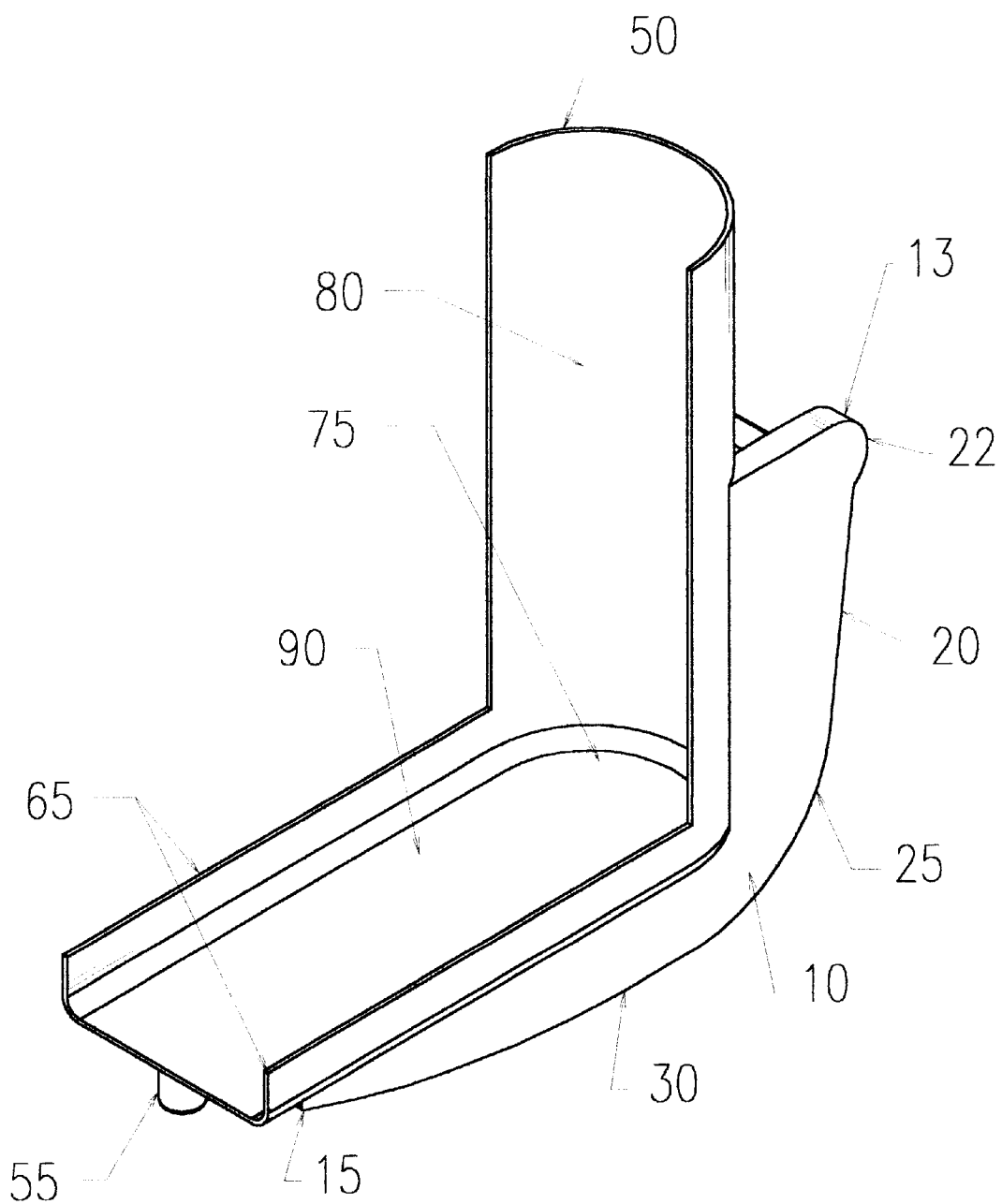
FIG. 2 depicts a preferred implementation of the invention.
Figure 3:
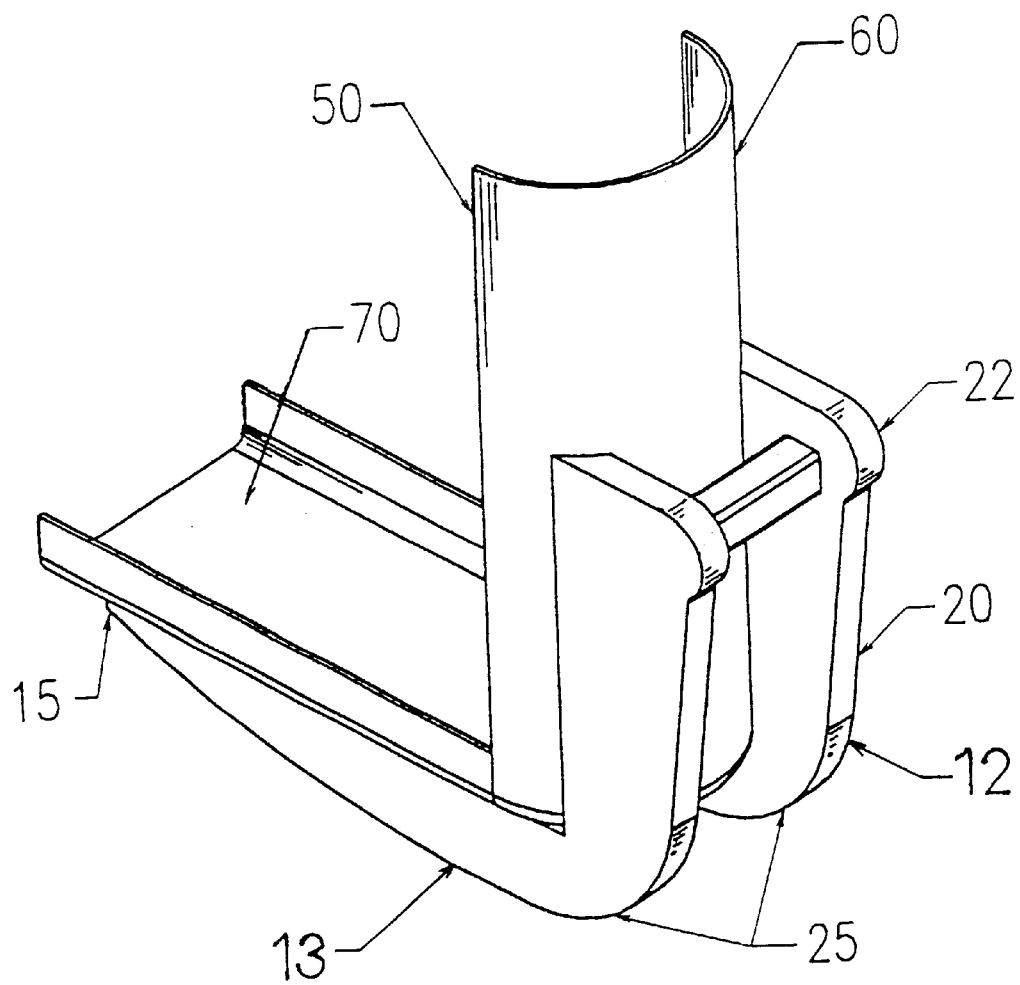
FIG. 3 depicts a rear isometric view of an implementation of the invention.
Figure 8:
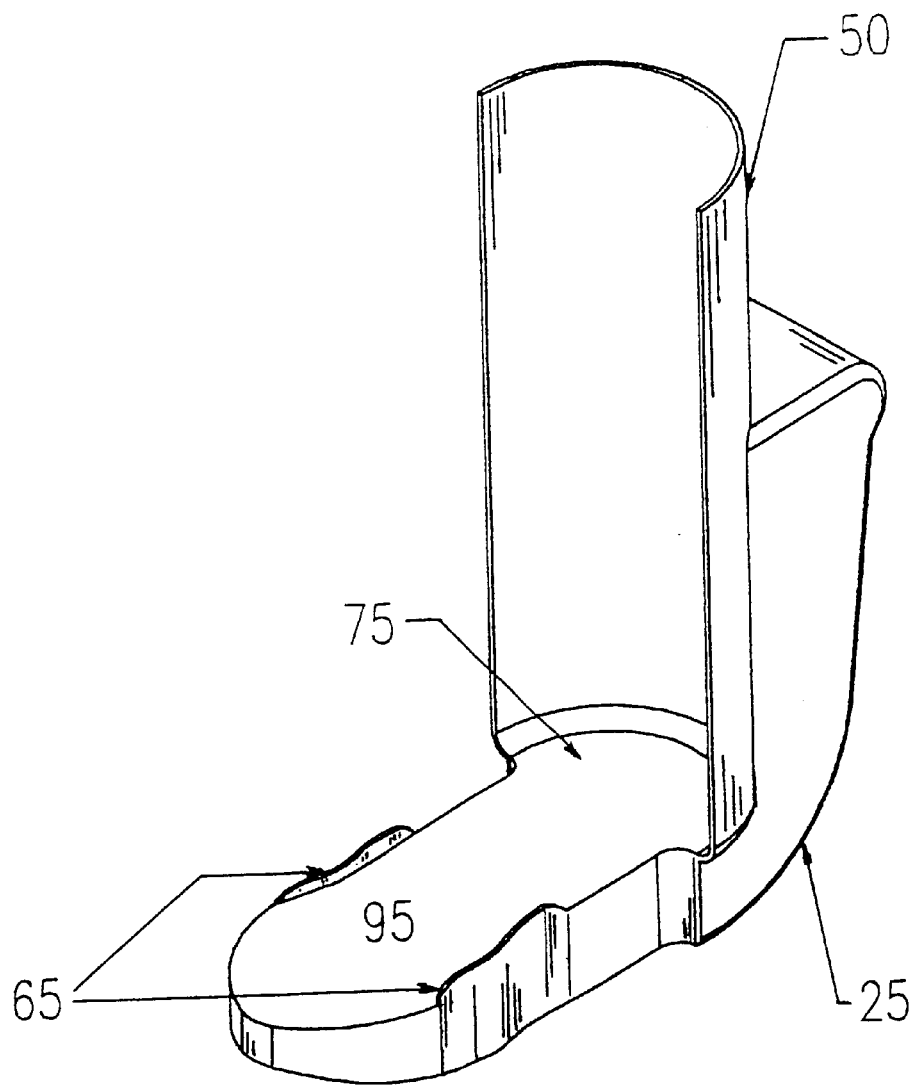
FIG. 8 depicts yet another embodiment of the invention showing a shoe shaped leg portion.

Referring now to FIGS. 1 and 2, an L-shaped channel 50 having a calf portion 80 and a foot portion 90 is visible. Calf portion 80 and foot portion 90 are joined at a joint 75. Preferably, the joint 75 has a rounded profile to better accommodate the heel of a shoe 150. The foot portion 90 is constructed of a slab 70 with sufficient width to receive a human shoe 150. Two parallel vertical sidewalls 65 attached to opposite sides of the slab 70 define the channel at the foot portion 90 and serve to prevent the shoe 150 from sliding off the foot portion 90. Alternatively, the foot portion 90 may comprise a shoe-shaped support 95, in which case the sidewalls 65 are not parallel but rather generally conforming to the shape of a shoe 150. Optionally, partially or fully constructing the foot portion 90 of flexible yielding material, springs embedded in the foot portion 90, molding at least a part of the foot portion 90 to conform to a shoe 150 shape (e.g. as shown in FIG. 8), utilizing a plurality of pegs to hold the shoe 150 in place, or other means, may be employed to hold the shoe 150 in place. Such implementation should also be construed as a channel for the purpose of the present invention, since they conform to the primary purpose of the channel, which is to maintain the shoe 150 in the desired, position while donning the AFO 100 and the shoe 150. All the above mentioned implementations and their equivalents, may be summed up as having the foot portion 90 comprise a molded shoe 150 support to conformally and yieldingly receive a shoe 150.

Preferably, the calf portion 80 is provided with a concave arcuate forward surface such as a semi-circle or elliptical cross section, to better fit the contours of an AFO 100 upper part, and thus serve to better stabilize an AFO 100 nestled therein. The calf portion 80 is also constructed wide enough to offer support for an AFO 100.

In the preferred implementation, a weight 55 is attached to the forward part 15 of the foot portion 90. The weight 55 causes a gravitational force to act on the device and thus urge the device to a rest position with the foot portion 90 being substantially parallel to the floor, and the calf portion 80 vertical. Achieving weight distribution to cause such bias may be carried out by adding a weight 55 to the foot portion as described, using different construction materials, making the foot portion 90 thicker, and other methods clear to a person skilled in the art.

A rocker 10 is attached to, or preferably integral to, the back side 60 of the calf portion 80, and extends at least to the back of the joint 75 area. The rocker 10 gives a rounded profile to the lower outer side of the joint 75 and forms a rail 25 to act as a ground interface surface. The rounded rail 25 serves as a cam to allow smooth rotation of the device to an inclined position. Preferably, the rocker 10 is molded into the back of the L channel 50 and more preferably, it comprises two roll bar sections 12 and 13, with similar profiles disposed substantially parallel to each other at laterally opposing sides of the L-shaped channel 50. This arrangement allows for a lighter, more stable device and less expensive construction.

The rocker 10 in the preferred implementation extends upward and backward from the joint 75 area, to form an upper extended rail 20 portion with extended ground interfacing surface. The extended rail 20 profile is also arcuate in form, but extends further rearwardly so as to increase the moment effects of the weight concentration 55 in the forward part of the foot portion 90. This construction increases the propensity of the device to maintain upright position at rest. Preferably, a protrusion 22 is located the upper part of the extended rail 20 to act as a roll stop to further reduce the risk of rolling over when the device is tilted. The roll stop is sufficiently large to stop the device from toppling over and lying on the ground on its calf portion 80 under normal operating conditions.

Optionally, the rocker 10 may also be extended along and below the foot portion 90 to any convenient length, to form a resting rail 30. If extended along the foot portion 90, the resting rail 30 preferably extends for a sufficient distance to allow the foot portion 90 to lie parallel to ground at rest. More preferably, the resting rail 30 is substantially flat, or includes one or more downward protrusions to support the device at rest into a desired position. Yet another desired feature is having the lower surface of the resting rail 30 comprise a high friction surface, commonly known as non-slip surface. Special needs may require a tall resting rail 30, and such resting rail 30 is thus contemplated herein and considered a part of one preferred implementation. It is however a desired feature of the preferred implementation to reduce the total height of the foot portion 90 above ground. Therefore, the resting rail 30 may be eliminated without detracting from the invention.

The preferred implementation calls for the rocker 10 to be integrally molded into the back side 60 of the L-shaped channel 50. A molded plastic, single piece unit is believed to be the most cost effective and allowing for the easy integration of the contour and weight distribution desired.

Figure 4:
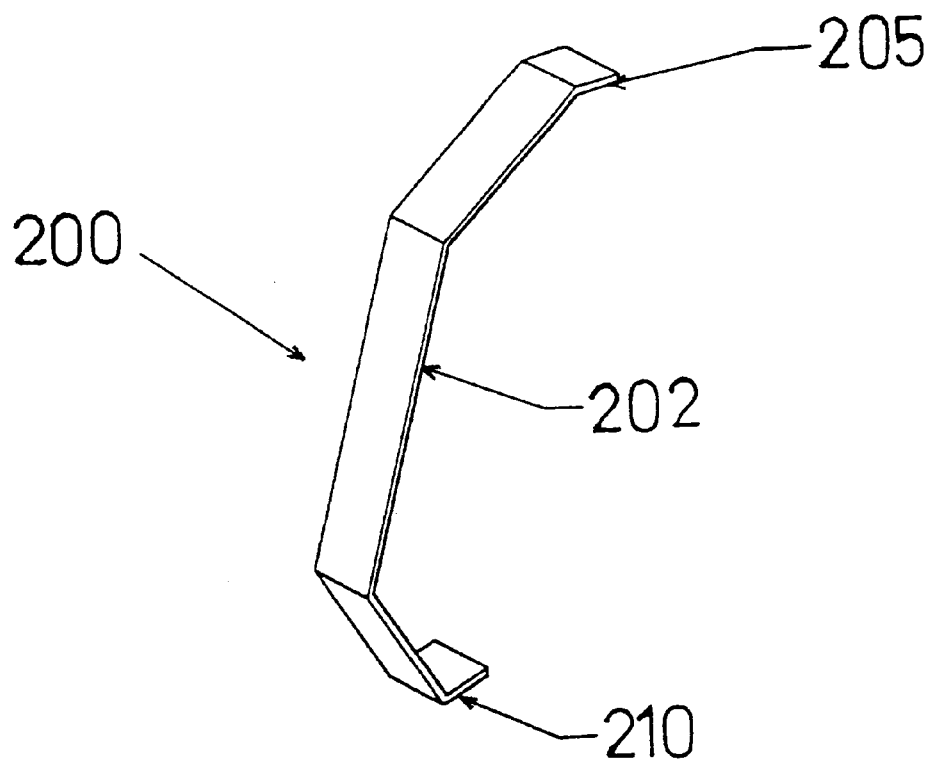
FIG. 4 depicts a preferred implementation of a shoe tongue retainer.

Due to difficulty in tying shoelaces, patients frequently use elastic shoelaces, Velcro fasteners or other elastic method for fastening the shoe 150, without shoelaces. The fastening arrangements and the shoe construction allow the tongue 155 to elastically return to its natural location after being bent forward to allow more convenient donning of the shoe 150. The present invention thus discloses an optional Shoe Tongue Retainer 200 to assist in maintaining the shoe tongue 155 out of the way as the foot is inserted into the shoe 150. Using such shoe tongue retainer 200 increases the opening size of the shoe 150 and affords easier donning of the shoe 150. The shoe tongue retainer 200 is preferably constructed of a resilient elongated clip portion having at one end a concave toe holder 210 constructed to engage the toe portion of a shoe 150, and a tongue hook 205 disposed at the its other end. The tongue hook 205 may comprise a hook, pincers, a bent portion of the rod, or any convenient means to engage the shoe tongue 155. In the preferred implementation the shoe tongue retainer 200 comprises a C-shaped flat metal spring, with an acute angle bend forming the tongue hook 205 and several bends or curves forming the toe holder 210, as can be seen for example in FIG. 4.

Figure 5:
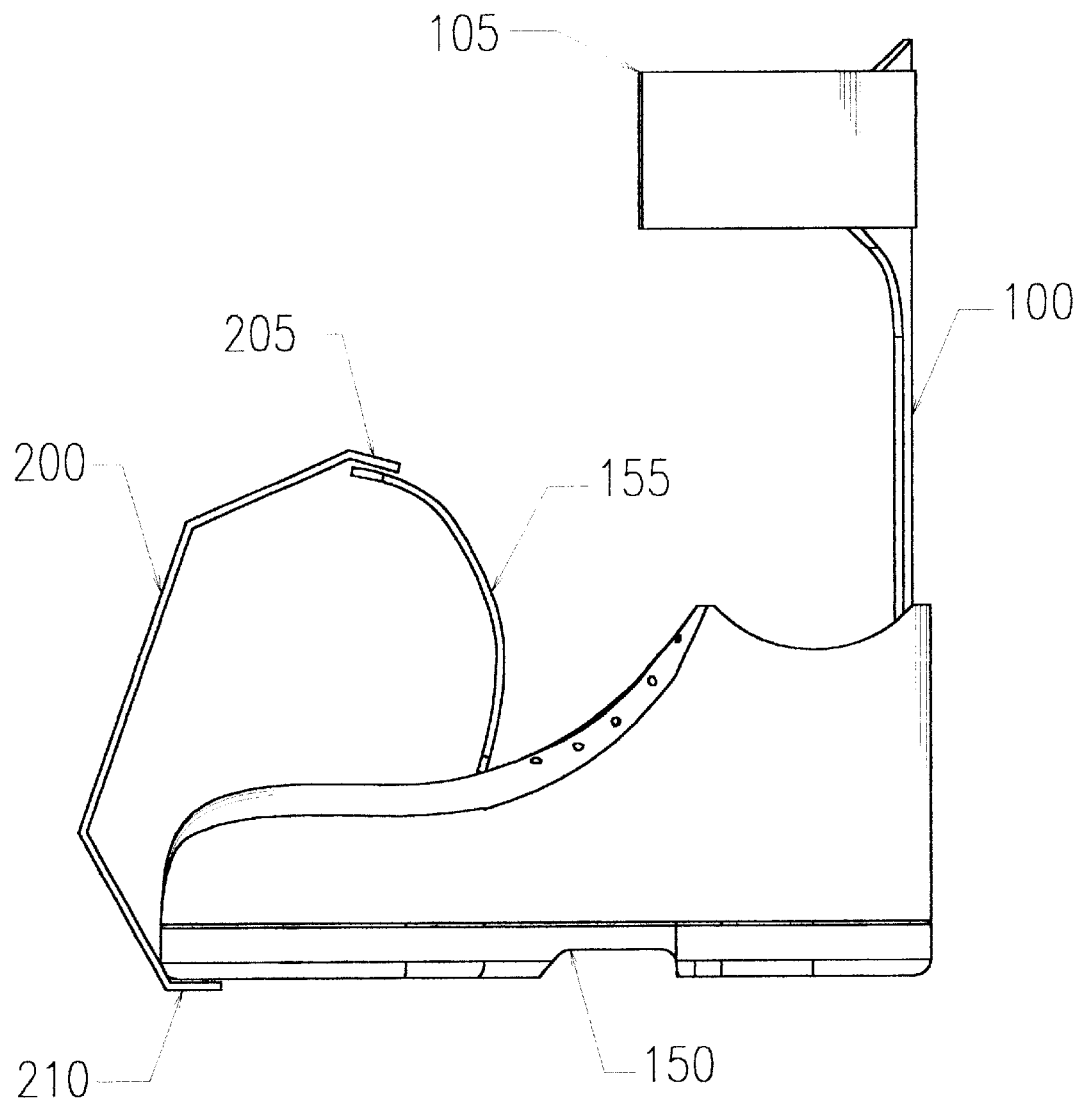
FIG. 5 depicts a deployed shoe tongue retainer.

In use, the patient inserts an AFO 100 into the shoe 150, and places the shoe 150 with the AFO 100 in the device so that the heel of the shoe 150 is near the joint 75. If desired, the shoe tongue retainer 200 is applied so that the toe holder 210 is pressed against the toe portion of the shoe 150, and the tongue 155 is bent or 'peeled' forward and engaged in the hook 205 so that the retainer yieldingly maintains the tongue 155 away from the shoe 150 opening as shown. The assembly of shoe 150, AFO 100 and shoe tongue retainer 200, ready for insertion into the L-shaped channel 50, is shown schematically in FIG. 5. The shoe 150/AFO 100 assembly is placed into the L-shaped channel 50 so that the shoe 150 sole fits generally over the foot portion 90, the heel of the shoe 150 fits into the joint area 75, and the calf portion of the AFO 105 rests in the calf portion 80 of the present invention. Preferably, the application of the shoe tongue retainer 200 is done prior to placing the shoe 150/AFO 100 in the channel 50. The channel 50 shape of the foot portion 90 prevents the shoe 150 from sliding sideways, and the channel 50 shape of the calf portion 80 prevents the AFO 100 from sliding sideways. Clearly, it is advantageous to construct the calf portion 80 with a concave arcuate forward surface to better maintain the position of the AFO 100, and thus the preferred implementation uses a calf portion 80 having at least in part thereof a semicircular cross section. In the alternative implementation described above, other means for maintaining the shoe 150 in the desired position may be employed, with, or as an alternative to the channel 50. Those means include, but are not limited to, springs, molding or otherwise manufacturing the foot portion 90 to conform to general shape of at least a portion of a shoe 150, protrusions placed strategically to hold the show 150 in place, elastic walls to yieldingly maintain the shoe 150, and any commonly known means to perform the function of supporting the shoe 150 while preventing it from swaying.

The placement of the shoe 150/AFO 100 assembly in the device is eased by using the calf portion 105of the AFO as a handle for the shoe 150/AFO 100 assembly, to thus overcome the need to bend, which is often difficult to a patient. In order to further ease placement, a strap or handle may be attached to the calf portion 80 to support the device, and alternatively to allow easy pick up of the device as a whole for placement of the shoe 150/AFO 100 therein and than to ease placement of the device on the ground.

Figure 6:
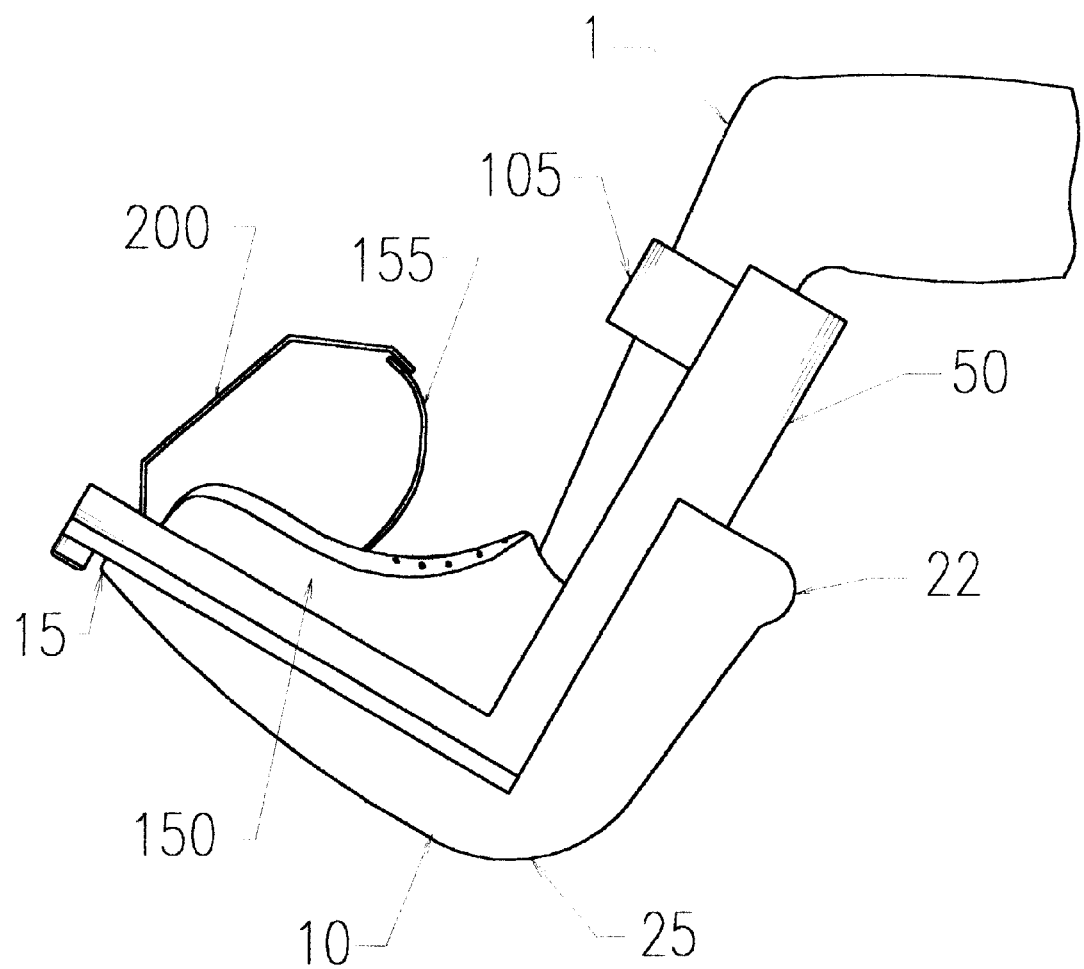
FIG. 6 depicts a preferred implementation of the invention showing a preferred use method thereof.
Figure 7:
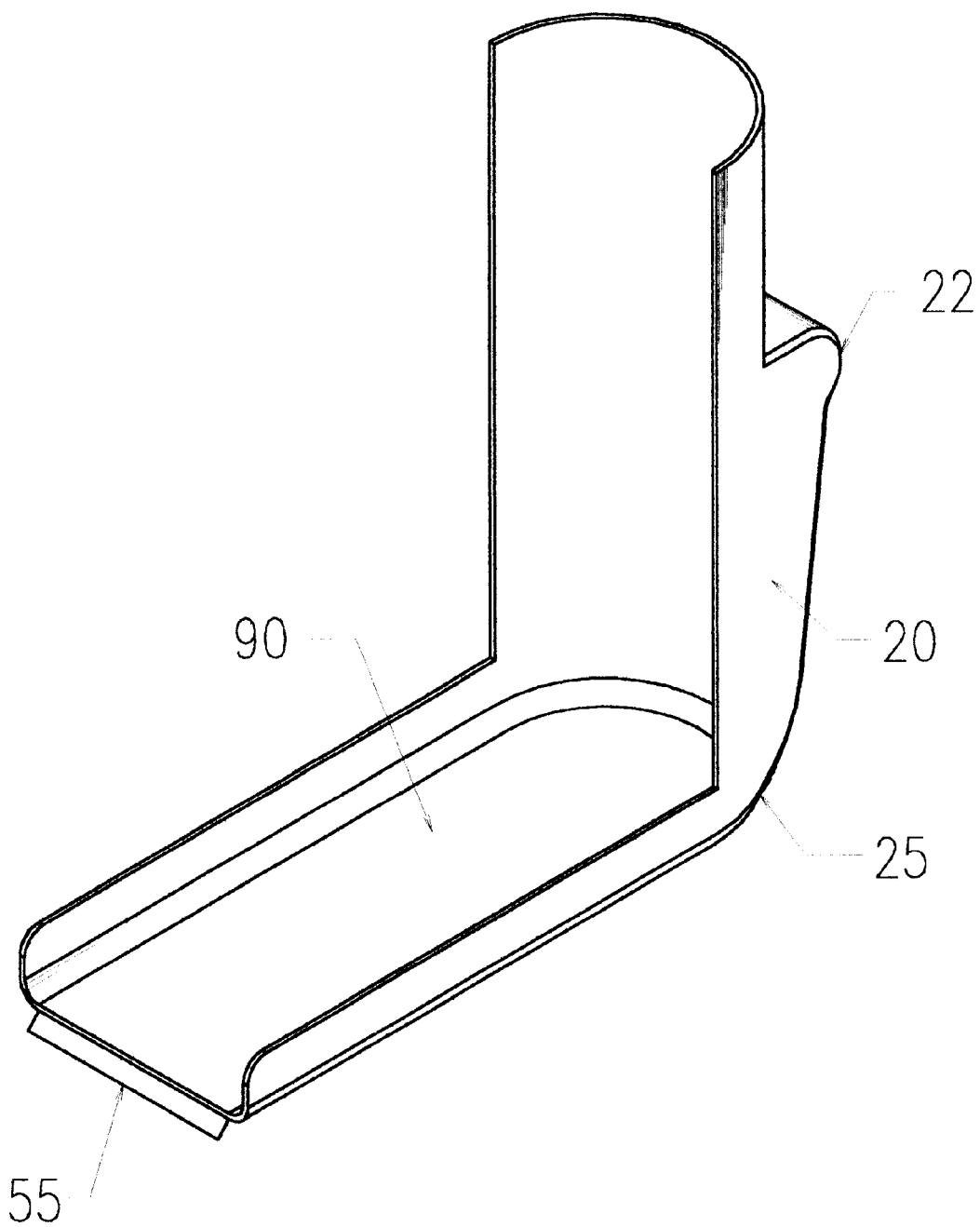
FIG. 7 depicts another preferred implementation of the invention showing an integral rocker.

FIG. 6 depicts an implementation of the device during use with the shoe 150/AFO 100 in the device and the device placed on the ground so that it rests on rail 25. The patient places his/her foot on the calf portion 80, preferably at its upper portion. The added weight causes the device to tilt about the cam-like surface of the roll rail 25 into an inclined position, and brings the shoe 150 to a comfortable angle to accept the foot, toes first, in an anatomically correct and comfortable manner. The AFO 100 and the channel-like calf portion 80 form a guide to ease the placement of the foot into the shoe 150. The patient can thus slide his/her foot into the shoe 150 comfortably and the guide naturally guides his/her foot into the shoe 150. After the foot is placed in the shoe 150, the strap of the AFO 100 may be tightened around the patient's calf and the leg removed from the device. The device then returns to its upright position due to the weight distribution discussed above. The shoe tongue retainer 200 is kicked or otherwise removed out of the way to allow the tongue 155 to elastically return to its natural position and complete donning the shoe 150.

It should also be noted that while the preferred implantation calls for a joint 75 formed at the joining area of the foot portion 80 and the calf portion 90, such a join may exist even if the foot portion and calf portion do not physically meet, but are kept apart from each other at a substantial orientation as described. In such case the area described inhere as the joint 75 is located where an extension of the foot and/or calf portions (90/80) meet either the other portion or its extension. Thus the invention is also aimed at such implementation where a portion of the L shaped channel 50 is missing.

While there have been described what are at present considered to be the preferred embodiments of this invention, it will be obvious to those skilled in the art that various other embodiments, changes, equivalents, and modifications, may be made therein without departing from the spirit or scope of this invention. It is therefore aimed to cover all such changes modifications and equivalents as fall within the true spirit and scope of the invention, and for which letters patent is applied.

What is claimed is:

1. An ankle foot orthosis donning device comprising:
   an L-shaped channel having a vertical calf portion and a forwardly extending horizontal foot portion joined to said calf portion at a joint;
   at least one rocker disposed proximally to said joint and extending rearwardly therefrom, said rocker comprising a convexly arcuate cylindrical rail contoured to act as a cam to allow substantially smooth rotation of said L-shaped channel into an inclined position when tilted; and
   wherein said foot portion is sufficiently weighted to bias said device to an upright position.

2. The device of claim 1 further comprising an extended rail extending rearwardly and upwardly of said joint, forming an eccentric cam, constructed to further bias the propensity of said device to return to an upright position at rest.

3. The device of claim 2 further comprising a rearwardly projecting protrusion disposed at the upper portion of said extended rail.

4. The device of claim 1 wherein said rocker further depends forwardly and downwardly of said joint to form a resting rail.

5. The device of claim 4 wherein said resting rail also having a lower surface comprising of high friction material.

6. The device of claim 1 wherein said calf portion channel is having a concave arcuate forward surface.

7. The device of claim 6 wherein said calf portion is further constructed with sufficient width and angularity to receive and maintain an upright portion of an ankle foot orthosis.

8. The device of claim 6 wherein said calf portion having a semicircular cross-section.

9. The device of claim 1 wherein said foot portion channel further comprises:

a shoe support slab of sufficient width to receive at least a portion of a shoe; and Two substantially vertical walls at opposing sides of said shoe support slab.

10. The device of claim 1 wherein said foot portion channel comprises a shoe support molded to yieldingly and conformally receive a shoe.

11. The device of claim 1 wherein said foot portion is constructed with large mass concentrated at the portion distal to said joint to affect said weighing thereof.

12. The device of claim 1 further comprising a weight attached to said foot portion to affect said weighting.

13. The device of claim 1 further comprising a shoe tongue retainer comprising:

An elongated clip portion having a first end and a second end;

a toe holder disposed at said first end; and, a tongue hook disposed at said second end.

14. The device of claim 1 further comprising a rearwardly projecting protrusion disposed at the upper portion of said rail.

15. An ankle foot orthosis donning device comprising:

an L-shaped channel having a vertical calf portion and a forwardly extending horizontal foot portion joined to said calf portion at a joint;

at least one rocker extending rearwardly and upwardly from said joint to at least a portion of said calf portion, and comprising a convexly arcuate cylindrical rail, forming an eccentric cam to allow substantially smooth rotation of said L-shaped channel into an inclined position when tilted; and wherein said foot portion is sufficiently weighted to bias said calf portion to an upright position.

16. An ankle foot orthosis donning device comprising:

an L-shaped channel having a vertical, semi circular cross section calf portion, and a forwardly extending horizontal foot portion joined to said calf portion at a joint;

at least one rocker extending rearwardly and upwardly from said joint to at least a portion of said calf portion, and comprising a convexly arcuate cylindrical rail, forming an eccentric cam to allow substantially smooth rotation of said L-shaped channel into an inclined position when tilted;

a roll stop protrusion projecting rearwardly disposed at the upper extremity of said rail; and wherein said foot portion is sufficiently weighted to bias said calf portion to an upright position.

17. The device of claim 16 further comprising a shoe tongue retainer comprising:

An elongated portion having a first end and a second end;

a concave toe holder disposed at said first end; and, a tongue hook disposed at said second end.

* * * * *